United States Patent [19]

Smith et al.

[11] 4,332,784

[45] Jun. 1, 1982

[54] DUAL ISOTOPE ASSAYS

[75] Inventors: Geoffrey F. W. Smith; Ralph A. J. Stevens; Benjamin Jacoby, all of Buckinghamshire, England

[73] Assignee: The Radiochemical Centre Limited, Buckinghamshire, England

[21] Appl. No.: 116,776

[22] Filed: Jan. 30, 1980

[30] Foreign Application Priority Data

Feb. 6, 1979 [GB] United Kingdom ............... 7904036

[51] Int. Cl.³ .................. G01N 33/56; G01T 1/00; G01N 33/60
[52] U.S. Cl. ..................................... 424/1; 23/230 B
[58] Field of Search .................... 424/1, 12; 23/230 B

[56] References Cited

U.S. PATENT DOCUMENTS 3,952,091 4/1976 Grunberg et al. ................. 424/1.5
4,016,250 4/1977 Saxena ................................ 424/1
4,115,065 9/1978 Bayly et al. ........................ 424/1
4,225,576 9/1980 Denning et al. .................... 424/1

OTHER PUBLICATIONS

Brown et al.; J. Nucl. Med., 18, #3, 300–304, 1977.
Girgis et al.; Nuclear Science Abstracts, vol. 26, #3, Feb. 15, 1972, Abstract 4672.
Mitsuma et al.; Biochem. Biophys. Res. Comm., vol. 46, #6, 2107–2113, 1972.

*Primary Examiner*—Christine M. Nucker
*Attorney, Agent, or Firm*—Wenderoth, Lind & Ponack

[57] ABSTRACT

Dual isotope assays for thyroid function are performed by carrying out a radio-immunoassay for two of thyroxine (T4), tri-iodothyronine (T3), thyroid stimulating hormone (TSH), and thyroxine binding globulin (TBG) wherein a version of one of the thyroid components, preferably T4 or T3 is labelled with Selenium-75 and the version of the other thyroid component is labelled with a different radionuclide, preferably Iodine-125.

9 Claims, 1 Drawing Figure

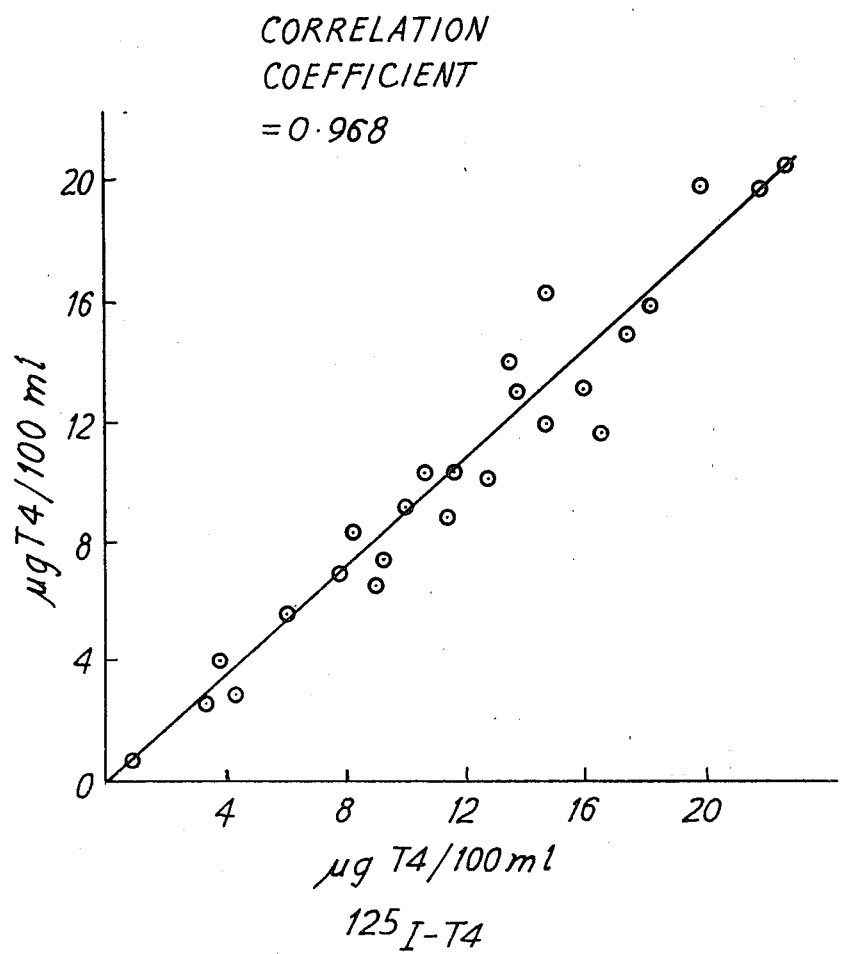

DUAL ISOTOPE ASSAYS

This invention relates to dual isotope tests of thyroid function.

The principal thyroid hormones are thyroxine (T4) and triiodothyronine (T3) whose circulating levels in the blood regulate metabolic processes. Output of these hormones from the thyroid gland are controlled by the levels of thyroid stimulating hormone (TSH) secreted by the pituitary gland. The greater part of the T4 and T3 in circulation is protein bound, the most important carrier being thyroxine binding globulin (TBG). The free hormone concentrations have been shown to correlate well with thyroid status. An imbalance of the thyroid hormones leads to severe distress in patients but, with correct diagnosis, treatment is very effective. A categorisation of patients into hypo-, eu-, and hyperthyroid states depends on the measurement of certain parameters in various combinations. More than one test is used because of the occurrence of borderline values, and the effects which age, pregnancy, disease, contraceptive and other drugs can have on measured values; reliance on a single test could result in mis-diagnosis.

The tests of thyroid function commonly used are estimations of total T4 and TSH or total T4 and T3, depending on the clinical situation. The most common means of assessing free T4 has been the Free Thyroxine Index (FTI), which is determined from measurements of total T4 and the spare binding capacity on TBG by a T3-uptake test. In those patients in whom measurements of binding proteins is indicated it may well be that the measurement of T3-uptake could be replaced by one of TBG, thus replacing the FTI value by a T4:TBG ratio.

In any clinical situation where it is required to measure two parameters it is obviously more economic if a dual parameter assay can be designed which requires only single operations for pipetting, incubation, centrifugation and counting instead of duplicate operations as would be the case for two independent assays. Dual parameter assays are made possible by the use of two isotopes differing in their gamma energies such that they may be counted simultaneously on a suitable gamma counter. Commercial dual isotope kits are now available which allow the simultaneous estimation of folate and vitamin $B_{12}$ by employing the isotopes iodine-125 and cobalt-57 respectively. In the thyroid field simultaneous determinations of T4 and T3 have been performed by utilising $^{125}$I-labelled thyroxine and $^{131}$I-labelled triiodothyronine (Hayes, S. P. and Goldie D. J., Ann. Clin. Biochem., (1977) 14, 12–15; Brown, M. L. et al., J. Nucl. Med., (1977) 18, 300–304). The application of this latter dual isotope assay is, however, severely limited by the relatively short 8-day half-life of iodine-131.

The present invention overcomes this disadvantage by providing a dual isotope test for thyroid function characterized in that the radioactively labelled version of one of the thyroid components being assayed is labelled with selenium-75. Thus the invention provides in one aspect a method of testing for thyroid function by performing a radio-immunoassay of a sample by a dual isotope technique known per se using versions of two of the thyroid components T4, T3, TSH and TBG labelled with two different radionuclides, characterized in that the version of one of the said thyroid components is labelled with Se-75.

The use of selenium-75 instead of iodine-131 to label one of the components to be assayed confers the very significant advantage of a long assay kit shelflife as a result of the long half-life of selenium-75 (118 days for $^{75}$Se versus 8 days for $^{131}$I). The performance of one $^{75}$Se-labelled thyroxine derivative, viz. the conjugate of thyroxine and 2-(methylseleno)-ethylamine-$^{75}$Se, has been compared with the $^{125}$I-T4 by substituting the $^{75}$Se-T4 ligand for the $^{125}$I-T4 ligand in a commercial assay kit (The Radiochemical Centre Limited, T4 RIA (PEG) kit, IM 92). FIG. 1 illustrates the correlation (correlation coefficient, 0.968) existing between the values obtained with the two different radioactive ligands.

For the dual isotope assays the techniques of radioimmunoassay as known in the art may be applied. Generally, mixed antisera to the two thyroid components being assayed plus the two radioactively labelled versions of the thyroid components are incubated in a single tube with either samples, e.g. of serum, being assayed or with mixed standards. As is well known, the amounts of thyroid component being assayed and of the labelled version thereof should together be more than sufficient for reaction with all the antibody provided, so that the thyroid component and its labelled version complete for reaction with the antibody. After incubation, the fraction of the thyroid component (plus its labelled version) bound to the antibody is separated from the fraction not so bound, e.g. by the addition of a suitable material known in the art to precipitate or adsorb one or other fraction. The radioactive concentration of the bound or the free, but preferably the bound, fraction is then counted. It is possible to effect this counting by passing the fraction twice through a gamma-radiation counter, the counter being set to detect gamma-radiation of different energy on each passage; but it is much preferred to use a dual channel counter. The peak energies of gamma-emission of Selenium-75 are found at 121, 136, 265 and 379 KeV, while the peak energies from Iodine-125 are found at 31 and 65 KeV, so it is a simple matter to adjust a counter to distinguish between the two.

The labelled version of the thyroid component may be chemically identical to the unlabelled component, as in the case where T3 or T4 is labelled with I-125, or may be chemically similar, as in the case where the component is labelled with Se-75. It is essential that the molecular configuration of the labelled version should be sufficiently similar to that of the unlabelled component so that the two may compete effectively with each other in the radioimmunoassay for reaction with antibody to the component. For this reason, it is desirable to avoid replacing the iodine atoms when labelling T3 or T4 with a foreign radionuclide, but rather to attach the radionuclide to the carboxylic acid or amino group of the molecule.

Preferred Se-75 derivatives of T3 and T4 for use in this invention have the formula:

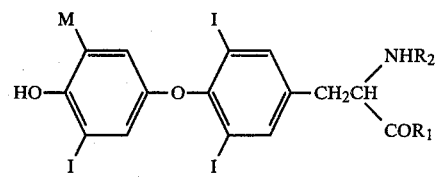

(a)

$R_1$ is OH or a carboxyl protecting group $R_2$ is $-CO-CX_1X_2X_3$ at least one of $X_1$, $X_2$ and $X_3$ is $-A_p(SeQ)_q$ A is saturated alkylene of 1 to 4 carbon atoms Q is alkyl or alkenyl of 1 to 6 carbon atoms, cycloalkyl, aryl or aralkyl, p is 0 or 1 q is 1 or 2 one of $X_1$, $X_2$ and $X_3$ may be amino or protected amino, one or two of $X_1$, $X_2$ and $X_3$ may be H M is H or I; or (b)

$R_2$ is H or an amino protecting group, $R_1$ is $-NZ-CY_1Y_2Y_3$ at least one of $Y_1$, $Y_2$ and $Y_3$ is $-A-(SeQ)_q$ one of $Y_1$, $Y_2$ and $Y_3$ may be $-COOH$ or protected carboxyl, one or two of $Y_1$, $Y_2$ and $Y_3$ may be H, Z is H or $-A-(SeQ)_q$ A is saturated alkylene of 1 to 4 carbon atoms, Q is alkyl or alkenyl of 1 to 6 carbon atoms, cycloalkyl, aryl or aralkyl, q is 1 or 2

M is H or I.

The following are examples of compounds that may be used to react with T3 or T4, or a derivative thereof in which either the carboxyl or the amino group is protected, in this way:

$CH_3SeCH_2CH_2NH_2$
$CH_3SeCH_2CH(NH_2)COOH$
$CH_3SeCH_2CH(SeCH_3)COOH$
$CH_3C(CH_2SeCH_3)_2COOH$
$(CH_3SeCH_2CH_2)_2NH$
$CH_3SeCH_2CH_2COOH$
$CH_3C(CH_2SeCH_3)_2NH_2$
$C_6H_5.CH_2SeCH_2CH_2COOH$
$C_6H_5.CH_2SeCH_2CH_2NH_2$

The selenium in these T3 and T4 derivatives contains an artificially high proportion of Se-75, such that the radioactive concentration of the derivative can be counted in a convenient time by conventional gamma-radiation counters.

The invention envisages dual-isotope assays inter alia in the following classes:

|  | Thyroid Variables Assayed | Variable Labelled with Se |
|---|---|---|
| Preferred | T3;T4 | T3 or T4 |
|  | T4;TSH | T4 |
|  | T4;TBG | T4 |
| Possible | T3;TSH | T3 |
|  | T3;TBG | T3 |

The invention envisages not only the determination of total T 4 (or total T 3) but also of free T 4 (or free T 3) in conjunction with the other entities mentioned. The determination of free T 4 in conjunction with TSH in a single dual isotope assay may be of special utility in the diagnosis of thyroid disease.

The labelled T3 and T4 derivatives may be prepared by methods known in the art. For example, isobutyl chloroformate is reacted with N-trifluoroacetyl T3 or T4 in the presence of a tertiary amine, the reaction being carried out at room temperature under anhydrous conditions in solvents such as dioxan and dimethylformamide in order to form the mixed anhydride. The mixed anhydride is subsequently reacted at room temperature in aqueous-organic media with the required selenoamine or selenoamino-acid or its ester, e.g. (2-methylseleno)-ethylamine or methylselenocysteine, to form an amide linkage between T3 or T4 and the seleno moiety. Instead of using isobutyl chloroformate to form the mixed anhydride the condensation of N-trifluoroacetyl T3 or T4 with either a selenoamine or selenoamino-acid may be effected in anhydrous solvents, e.g. dioxan or dimethylformamide, with reagents such as dicyclohexylcarbodiimide (DCC) or N-ethoxycarbonyl-2-ethoxydihydro-quinoline (EEDQ). Alternatively, these procedures using DCC and EEDQ may be used to couple a T3 or T4 alkyl ester via its free amino group to a selenocarboxylic acid or a selenoamino-acid. Cleavage of protecting groups may be effected by known hydrolytic procedures. Final products are isolated by preparative thin-layer chromatography on silica gel.

The selenoamines, selenoamino-acids, and selenocarboxylic acids, used to synthesize the T3 or T4 derivatives, may be prepared by methods known in the art. For example, solutions of sodium alkyl, alkenyl, cycloalkyl, aryl or aralkyl selenides are prepared by reacting the appropriate halogen compounds with disodium diselenide in anhydrous liquid ammonia, and subsequently cleaving the organic diselenides so formed with metallic sodium. The sodium alkyl, alkenyl, cycloalkyl, aryl or aralkyl selenides are then further reacted in anhydrous liquid ammonia with suitable halogen derivatives of amines, amino-acids or carboxylic acids to form the required products.

The following Examples illustrate the invention. Examples 1 to 3 relate to the preparation of Se-75 derivatives of T4, and Examples 4 to 6 show three different kinds of dual isotope assays employing the product of Example 1. Example 7 relates to T3.

EXAMPLE 1

(i) Preparation of N-trifluoroacetyl thyroxine

Thyroxine (240.6 mg; 0.310 mmoles) was suspended in trifluoroacetic anhydride (3 ml) and the mixture stirred under reflux for 4 hours. The trifluoroacetic anhydride was removed by evaporation in vacuo and the residue was dissolved in methanol (ca. 5 ml). On addition of water (20 ml) to the methanolic solution a precipitate formed, which was separated by centrifugation, washed with water (3×20 ml), and then dried in vacuo. Yield of N-trifluoroacetyl thyroxine, ca. 200 mg.

(ii) Preparation of 2-(methylseleno)-ethylamine-$^{75}$Se

Sodium selenite-75Se (2.71 Ci; 21.7 Ci/matom) in acid solution was treated with sulphur dioxide to precipitate red selenium-75Se, which after washing with water was transferred to a reaction tube and dried in vacuo. Yield, 2.48 Ci of red selenium-$^{75}$Se. The selenium-$^{75}$Se was suspended in anhydrous liquid ammonia and treated with sodium metal (3.1 mg; 0.135 matom) to produce a solution of disodium diselenide-$^{75}$Se. Excess methyl iodide (22.2 mg; 0.156 m mole) was added to form dimethyl diselenide-$^{75}$Se, which was cleaved by the further addition of sodium to form sodium methyl selenide-$^{75}$Se. 2-Bromoethylamine hydrobromide (22.8 mg; 0.111 mmol) was added to the reaction mixture which was then stirred until the ammonia had evaporated. The residue was held under vacuum for some time to remove volatile impurities, dissolved in water, and purified by preparative thin layer chromatography on silica gel (Eluent: butan-1-ol, acetic acid, water 60:15:25). The required zone was located by auto-radiography and the product recovered from the silica gel. Yield of 2-(methylseleno)-ethylamine-$^{75}$Se, 280 mCi.

(iii) Preparation of conjugate of thyroxine and 2-(methylseleno)-ethylamine-$^{75}$Se To N-trifluoroacetyl thyroxine (32.5 mg; $3.72 \times 10^{-2}$ mmol) dissolved in dry dimethylformamide (500 μl) was added dry triethylamine (5 μl; $3.59 \times 10^{-2}$ mmol) and isobutyl chloroformate (5 μl; $3.81 \times 10^{-2}$ mmol). After 3 minutes, 125 μl of this mixture was added to a solution of 2-(methylseleno)-ethylamine-$^{75}$Se (28.6 mCi; 21 Ci/mmol; $1.36 \times 10^{-3}$ mmol) in a mixture of dimethylformamide (1000 μl), water (500 μl) and triethylamine (10 μl). The reaction mixture was stirred at room temperature overnight, and after evaporation of volatile materials in vacuo the residue was treated with aqueous sodium hydroxide (1.2 ml of 1.16 N) at 70°-75° C. for 45 minutes. Water was evaporated and the lyophilized product was dissolved in methanol (500 μl) prior to purification by preparative thin layer chromatography on silica gel using chloroform, methanol, formic acid (80:15:5) as the developing eluent. Radioactive zones were located by autoradiography. The zone at $R_f$ ca. 0.5 was removed from the plate and the product eluted from the silica gel by successively washing with ammonium hydroxide solution in 50 percent aqueous ethanol (2 ml of N), and water ($4 \times 2$ ml). The final solution was filtered to remove silica particles. Yield of $^{75}$Se-labelled thyroxine conjugate, 3.3 mCi. The purification process removes unreacted thyroxine. Accordingly, the specific activity of the product was 21 Ci/mmol.

EXAMPLE 2

(i) Preparation of Se-methyl-L-selenocysteine methyl ester-$^{75}$Se

Se-methyl-L-selenocysteine-$^{75}$Se (151 mg; 0.83 mmol; 26 mCi/mmol) was refluxed in methanolic hydrogen chloride for 30 minutes. Methanol was evaporated and the process repeated on the residue. After removal of methanol the lyophilized product was treated with dilute aqueous sodium bicarbonate, and the methyl ester was extracted from the mixture into chloroform. The chloroform solution was dried over anhydrous sodium sulphate and the solvent then evaporated to yield Se-methyl-L-selenocysteine methyl ester-$^{75}$Se as an oil.

(ii) Preparation of conjugate of thyroxine and Se-methyl-L-selenocysteine methyl ester-$^{75}$Se Se-methyl-L-selenocysteine methyl ester-$^{75}$Se (47 mg; 0.24 mmol; 19.4 mCi/mmol) was dissolved in dry dioxan (10 ml). 2 ml of this solution was added to a mixture of N-trifluoroacetyl thyroxine (33.5 mg; 0.0383 mmol) and dicyclohexylcarbodiimide (20 mg; 0.097 mmol) in dry dioxan (3 ml), and the reaction mixture stirred at room temperature for 24 hours. After removal of dioxan in vacuo the crude product was dissolved in methanol (500 μl) and purified by preparative thin layer chromatography on silica gel using ethyl acetate, methanol (4:1) as the developing eluent. The product was isolated from a UV absorbing radioactive zone near the solvent front. Yield, 147 μCi of $^{75}$Se-labelled thyroxine conjugate.

EXAMPLE 3

(i) Preparation of β-selenocyanatopropionic acid-$^{75}$-Se

Red selenium-$^{75}$Se (366.7 mg; 4.46 matom; 0.526 mCi/matom) was dissolved in ca 3 ml of water containing potassium cyanide (301.2 mg; 4.63 mmol). After one hour the mixture was filtered to yield a solution of potassium selenocyanate-$^{75}$Se (2.07 mg; 3.93 mmol). β-propiolactone (3.09 mg; 4.27 mmol) was added to the solution, and the mixture stirred for one hour, acidified with hydrochloric acid, and allowed to stand overnight. It was then centrifuged and the supernatant was extracted with diethyl ether ($2 \times 25$ ml). The ether was evaporated from the extract to yield β-selenocyanatopropionic acid-$^{75}$Se (254 mg; 1.43 mmol).

(ii) Preparation of benzylselenopropionic acid-$^{75}$Se

β-selenocyanatopropionic acid-$^{75}$Se (254 mg; 1.43 mmol) in ethanol (2 ml) was added dropwise with stirring to a mixture of sodium borohydride (191 mg; 5.50 mmol) and benzyl chloride (198 mg; 1.56 mmol) in 6 ml of ice-cold ethanol. After 1½ hours the reaction mixture was treated with 2 ml of acetone and a few drops of concentrated hydrochloric acid to destroy excess borohydride. Evaporation of solvents from the mixture yielded an oil, which was partitioned between ether and aqueous sodium hydrogen carbonate solution. The aqueous phase was acidified and re-extracted with ether. Evaporation of this ether phase yielded radiochemically pure benzylselenopropionic acid-$^{75}$Se.

(iii) Preparation of conjugate of thyroxine methyl ether and benzylselenopropionic acid-$^{75}$Se Thyroxine methyl ester (38.5 mg; 0.049 mmol), dicyclohexylcarbodiimide (22.8 mg; 0.11 mmol) and benzylselenopropionic acid-$^{75}$Se (20.8 mg; 0.086 mmol; 0.52 mCi/mmol) were stirred overnight in 10 ml of dry dioxan. The mixture was evaporated to dryness and the product examined by TLC in several solvent systems. In all cases a radioactive component was detected in addition to the unreacted thyroxine methyl ester and benzylselenopropionic acid-$^{75}$Se.

The product was redissolved in dioxan, the solution centrifuged, and the supernatant then applied to a preparative silica gel TLC plate. The plate was developed with chloroform, methanol (10:1) and the component of $R_f$ ca 0.9 was isolated by eluting the silica gel zone with ethanol. After evaporation of the ethanol the product was examined by infra red spectroscopy: the spectrum was consistent with the structure of T4 methyl ester/benzylselenopropionic acid conjugate. Yield 7.3 μCi.

EXAMPLE 4

Dual Isotope Assay of T4 and T3

(a) Preparation of reagents and standards:
 (i) Antisera:
  Mixed antisera to T4 and T3 was prepared at the appropriate dilutions in a barbitone/acetate buffer containing 0.625% thiomersalate (a commonly used agent for blocking the binding of T4 to TBG).
 (ii) Radioactive labels:
  Mixed $^{75}$Se-T4 (the conjugate of T4 with 2-(methylseleno)-ethylamine-$^{75}$Se prepared as in Example 1) and $^{125}$I-T3 was prepared in barbitone/acetate buffer containing 0.625% thiomersalate.
 (iii) Standards:
  Human serum standards with calibrated values of T4 and T3 were used.
(b) Protocol:
 50 μl of serum (either samples or standards) was incubated with 200 μl of mixed radioactive labels and 200 μl of mixed antisera for 1 hour at 37° C. The reaction was terminated and antibody-bound T4 and T3 were precipitated by the addition of 1 ml of polyethylene glycol 6000 (20% w/v in water). The reaction tubes were then centrifuged and the supernatants decanted.

(c) Dual isotope counting:

Precipitates were counted on a dual channel gamma counter with windows set at 10–90 keV for $^{125}$I and 90–480 keV for $^{75}$Se.

The values obtained from the dual isotope assay were compared with those obtained from two independent assays using the same reagents but only a single radioactive label, i.e. either $^{75}$Se-T4 or $^{125}$I-T3 (see Table 1).

TABLE 1

| | Comparison of dual and single isotope assays for T4 and T3 | | | |
|---|---|---|---|---|
| | T4 (μg/100ml) | | T3 (ng/ml) | |
| Control Serum | Dual Assay | Single Assay | Dual Assay | Single Assay |
| A | 2.4 | 2.5 | 0.2 | 0.2 |
| C | 12.3 | 13.5 | 2.0 | 1.9 |
| G | 4.7 | 4.9 | 2.2 | 2.8 |
| H | 1.6 | 1.5 | 0.4 | 0.4 |
| J | 7.0 | 7.2 | 1.6 | 1.5 |

EXAMPLE 5

Dual Isotope Assay of T4 and TSH (a) Preparation of reagents and standards:

(i) TSH antiserum and $^{75}$Se-T4 label:

TSH antiserum and $^{75}$-Se-T4 label (the conjugate of T4 with 2-(methylseleno)-ethylamine-$^{75}$Se prepared as in Example 1) were mixed in appropriate concentrations in a barbitone/acetate buffer containing 0.625% thiomersalate.

(ii) $^{125}$I-TSH label and T4 antiserum:

$^{125}$I-TSH label and T4 antiserum were mixed at the appropriate concentrations in a barbitone/acetate buffer containing 0.625% thiomersalate. This reagent also contained carrier rabbit and sheep serum to provide an adequate precipitate in the presence of second antibody.

(iii) Standards:

Human serum standards with calibrated values of T4 and TSH were used.

(iv) Second antibody:

Second antibody, raised in donkey against rabbit and sheep immuno-globulin fractions, was diluted to an optimised concentration in barbitone/acetate buffer.

(b) Protocol:

200 μl of serum (either samples or standards) were incubated with 100 μl of reagent (i) for 2 hours. To this was added 100 μl of reagent (ii) and the mixture incubated for a further 2 hours. 100 μl of second antibody was added and after 10 minutes addition of 1 ml of ammonium sulphate (199 g/l) was made. The reaction tubes were centrifuged and the supernatants decanted.

(c) Dual Isotope Counting:

Precipitates were counted as in Example 4.

Again as in Example 4 the values obtained from the dual isotope assay were compared with those obtained from two independent assays using the same reagents but only a single radioactive label, either $^{75}$Se-T4 or $^{125}$I-TSH (see Table 2).

TABLE 2

| | Comparison of dual and single isotope assays for T4 and TSH | | | |
|---|---|---|---|---|
| | T4 (μg/100ml) | | TSH (μU/ml, MRC 68/38) | |
| Control Serum | Dual Assay | Single Assay | Dual Assay | Single Assay |
| B | 6.5 | 6.4 | 5.1 | 5.6 |
| C | 6.7 | 6.7 | 7.5 | 7.3 |
| D | 6.6 | 6.5 | 25.5 | 28.7 |
| T4 A | 3.8 | | 3.2 | 3.4 |
| T4 C | 5.0 | | 13.1 | 13.9 |

EXAMPLE 6

Dual Isotope Assay of T4 and TBG (a) Preparation of reagents and standards:

(i) Binding reagent:

TBG binding reagent was prepared to give an overall 1% sheep serum and 6.4% donkey second antibody in barbitone buffer containing 0.625% thiomersalate, the sheep component containing an optimised amount of TBG antiserum. T4 binding reagent was similarly prepared to give 0.2% sheep serum, containing an optimised amount of T4 antiserum, and 1.5% of donkey second antibody. Both reagents were separated by centrifugation, washed by suspension in the same buffer and recentrifugation, and finally combined at optimised concentrations in barbitone buffer containing 0.625% thiomersalate.

(ii) Radioactive labels:

Mixed $^{75}$Se-T4 (the conjugate of T4 with 2-(methylseleno)-ethylamine-$^{75}$Se prepared as in Example 1) and $^{125}$I-TBG were prepared in barbitone buffer containing 0.625% thiomersalate.

(iii) Standards:

Human serum standards with calibrated values of T4 and TBG were used.

(b) Protocol:

50 μl of serum (either samples or standards) was incubated with 500 μl of mixed radioactive labels and 1 ml of binding reagent for 2 hours. The mixture was then centrifuged and the supernatant decanted.

(c) Dual Isotope Counting:

Precipitates were counted as in Example 4.

The values obtained from the dual isotope assay were compared with those obtained from two independent assays in which a single binding reagent and the appropriate label were used (see Table 3).

TABLE 3

| | Comparison of dual and single isotope assays for T4 and TBG | | | |
|---|---|---|---|---|
| | T4 (μg/100 ml) | | TBG (mg/l) | |
| Serum | Dual Assay | Single Assay | Dual Assay | Single Assay |
| M$_1$ | 5.4 | 6.2 | 16.3 | 16.3 |
| M$_2$ | 5.9 | 7.1 | 20.3 | 20.0 |
| M$_3$ | 4.0 | 4.6 | 12.3 | 13.0 |

EXAMPLE 7

(i) Preparation of N-trifluoroacetyl triiodothyronine

Triiodothyronine (456.7 mg) was suspended in trifluoroacetic anhydride (20 ml) and the mixture stirred under reflux for 4½ hours. The trifluoroacetic anhydride was removed by evaporation under reduced pressure.

The residue was washed with water (3×25 ml) and then dried in vacuo. Yield of N-trifluoroacetyl triiodothyronine, 341.3 mg.

(ii) Preparation of conjugate of triiodothyronine and 2-(methylseleno)-ethylamine-$^{75}$Se To N-trifluoroacetyl triiodothyronine (24.0 mg; 3.21×10$^{-2}$ mmol) dissolved in dry dimethylformamide (500 μl) was added dry triethylamine (5 μl; 3.59×10$^{-2}$ mmol) and isobutylchloroformate (5 μl; 3.81×10$^{-2}$ mmol). After 30 seconds 200 μl of this mixture was added to a solution of 2-(methylseleno)-ethylamine-$^{75}$Se (22.9 mCi; 17.4 Ci mmol; 1.31×10$^{-3}$ mmol) in a mixture of dimethylformamide (700 ml) and water (700 ml). The reaction mixture was diluted with 500 μl of dimethylformamide, stirred for one hour and allowed to stand at room temperature overnight. Volatile materials were removed from the mixture by evaporation in vacuo and the residue was treated with aqueous-ethanolic sodium hydroxide (1 ml of ethanol, 2 N aqueous sodium hydroxide (1:1)) at 80° C. for 40 minutes. After the addition of 3 N hydrochloric acid (350 μl) solvents were evaporated in vacuo. The lyophilized product was dissolved in methanol (350 μl) and the solution applied to a preparative silica gel TLC plate which was developed with chloroform, methanol, formic acid (80:15:5). Radioactive zones were located by autoradiography. The zone at Rf ca 0.4 was removed from the plate and the product eluted from the silica gel with aqueous-ethanolic ammonium hydroxide. Yield of $^{75}$-Se-labelled triiodothyronine conjugate, 126 μCi.

(iii) Binding of triiodothyronine/2-(methylseleno)ethylamine-$^{75}$Se conjugate ($^{75}$Se-T3) to T3 antiserum T3 antiserum (titre for T3 radioimmunoassay, 220,000) was diluted to a 1% solution in barbitone buffer containing 0.625% thiomersalate, pH 8.6. 50 μl of $^{75}$Se-T3 solution (126 μCi/8 ml; 17.4 Ci/mmol) was diluted to 10 ml with the same barbitone buffer to provide Label Reagent 1 (4.5 nM concn. of $^{75}$Se-T3); a further 10-fold dilution of Label Reagent 1 with buffer provided Label Reagent 2 (0.45 nM concn. of $^{75}$Se-T3).

50 μl of resin-treated serum (free of T3) was incubated with 200 μl of antiserum reagent and 200 μl of Label Reagent (either 1 or 2). As a control a similar incubation was set up using a dilute solution of $^{125}$I-T3 in place of the $^{75}$Se-T3 label. Antiserum-bound labels were precipitated by the addition of 1 ml of polyethylene glycol and then separated by centrifugation. Supernatants were decanted and the precipitates counted.

Reagent: $^{75}$Se-T3 (1), $^{75}$Se-T3 (2), $^{125}$I-T3,
% Bound: 47.9, 54.8, 51.6.

We claim:

1. A method of testing for thyroid function by performing a radio-immunoassay of a sample by a dual isotope technique comprising the steps:
    (a) mixing the sample to be assayed with a version of a first thyroid component selected from the group T3, T4, TSH and TGB labelled with Se-75 and a version of a second thyroid component selected from the said group labelled with another radioactive isotope, and with an antibody to the said first component and an antibody to the said second component, the amount of antibody being in each case insufficient for reaction with all the thyroid component and labelled version thereof that are present,
    (b) incubating the mixture to effect reaction between the thyroid components and the labelled versions thereof, and their respective antibodies,
    (c) separating the fractions of the thyroid components plus the labelled versions thereof that are bound to the antibodies from the fractions not so bound,
    (d) measuring the radioactive concentrations of the bound or the unbound fractions, and
    (e) using the measurements to calculate the concentrations of the thyroid components in the sample being assayed.

2. The method as claimed in claim 1, wherein the version of the other of the said thyroid components is labelled with I-125.

3. The method as claimed in claim 1, wherein T3 or T4 is labelled with Se-75, the version thereof having the formula:

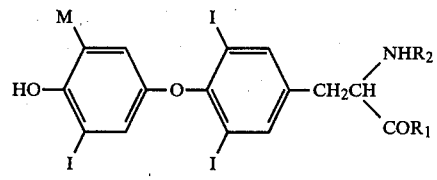

(a)
    R$_1$ is OH or a carboxyl protecting group
    R$_2$ is -CO-CX$_2$X$_2$X$_3$
    at least one of X$_1$, X$_2$ and X$_3$ is -A$_p$(SeQ)$_q$
    A is saturated alkylene of 1 to 4 carbon atoms
    Q is alkyl or alkenyl of 1 to 6 carbon atoms, cycloalkyl, aryl or aralkyl,
    p is 0 or 1
    q is 1 or 2
    one of X$_1$, X$_2$ and X$_3$ may be amino or protected amino,
    one or two of X$_1$, X$_2$ and X$_3$ may be H
    M is H or I; or
(b)
    R$_2$ is H or an amino protecting group,
    R$_1$ is -NZ-CY$_1$Y$_2$Y$_3$
    at least one of Y$_1$, Y$_2$ and Y$_3$ is -A-(SeQ)$_q$
    one of Y$_1$, Y$_2$ and Y$_3$ may be -COOH or protected carboxyl,
    one or two of Y$_1$, Y$_2$ and Y$_3$ may be H
    Z is H or -A-(SeQ)$_q$
    A is saturated alkylene of 1 to 4 carbon atoms,
    Q is alkyl or alkenyl of 1 to 6 carbon atoms, cycloalkyl, aryl or aralkyl,
    q is 1 or 2
    M is H or I.

4. The method as claimed in claim 3, wherein, in alternative (a), R$_2$ is selected from
    CH$_3$.SeCH$_2$.CH(NH$_2$).CO—
    CH$_3$.SeCH$_2$.CH(SeCH$_3$).CO—
    CH$_3$.C(CH$_2$.SeCH$_3$).CO—
    CH$_3$.SeCH$_2$.CH$_2$.CO—
    C$_6$H$_5$.CH$_2$.SeCH$_2$.CH$_2$.CO—.

5. The method as claimed in claim 3, wherein, in alternative (b), R$_1$ is selected from
    CH$_3$.SeCH$_2$.CH$_2$.NH—
    (CH$_3$.SeCH$_2$.CH$_2$)$_2$.N—
    CH$_3$.C(CH$_2$.SeCH$_3$)$_2$.NH—
    C$_6$H$_5$.CH$_2$.SeCH$_2$.CH$_2$.NH—.

6. The method as claimed in claim 1, wherein the said first and second thyroid components are selected from the following combinations:

| FIRST COMPONENT | SECOND COMPONENT |
|---|---|
| T3 | T4 |
| T4 | T3 |
| T4 | TSH |
| T4 | TBG |
| T3 | TSH |
| T3 | TBG. |

7. The method as claimed in claim 1, comprising the steps:
 (a) mixing the sample to be assayed with a version of T4 labelled with Se-75 and a version of a selected member of the group T3, TSH and TBG labelled with I-125, and with an antibody to T4 and an antibody to the selected member of the group T3, TSH and TBG, the amount of antibody being in each case insufficient for reaction with all the thyroid component and labelled version thereof that are present,
 (b) incubating the mixture to effect reaction between the thyroid components and the labelled versions thereof, and the antibodies,
 (c) separating the fractions of the thyroid components plus the labelled versions thereof that are bound to the antibodies from the fractions not so bound,
 (d) measuring the radioactive concentrations of the bound or the unbound fractions, and
 (e) using the measurements to calculate the concentrations of the thyroid components in the sample being assayed.

8. The method as claimed in claim 7, wherein step (d) is performed by a single passage of the fraction through a dual chamber counter.

9. The method according to claim 7 in which at least one thyroid component is pre-incubated with its antibody before admixture with the labelled version of the said component.

* * * * *